(12) United States Patent
Tanaka et al.

(10) Patent No.: US 12,396,701 B2
(45) Date of Patent: Aug. 26, 2025

(54) X-RAY IMAGING APPARATUS AND POSITIONAL DEVIATION DETECTION UNIT FOR X-RAY IMAGING APPARATUS

(71) Applicant: SHIMADZU CORPORATION, Kyoto (JP)

(72) Inventors: Masato Tanaka, Kyoto (JP); Masahiro Hibi, Kyoto (JP); Hiroyuki Kinoshita, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 102 days.

(21) Appl. No.: 17/523,978

(22) Filed: Nov. 11, 2021

(65) Prior Publication Data
US 2022/0202388 A1    Jun. 30, 2022

(30) Foreign Application Priority Data

Dec. 25, 2020 (JP) ................. 2020-217397

(51) Int. Cl.
*A61B 6/08* (2006.01)
*A61B 6/00* (2006.01)
(Continued)

(52) U.S. Cl.
CPC ............. *A61B 6/587* (2013.01); *A61B 6/08* (2013.01); *A61B 6/4283* (2013.01);
(Continued)

(58) Field of Classification Search
CPC ....... A61B 6/0492; A61B 6/08; A61B 6/4283; A61B 6/4405; A61B 6/4411;
(Continued)

(56) References Cited

U.S. PATENT DOCUMENTS

| 5,241,578 A | * | 8/1993 | MacMahon | ............... G21K 1/02 378/154 |
| 5,517,546 A | * | 5/1996 | Schmidt | .................. A61B 6/587 378/205 |

(Continued)

FOREIGN PATENT DOCUMENTS

| JP | 2013-523396 A | 6/2013 |
| JP | 2015077251 A | * 4/2015 |

(Continued)

OTHER PUBLICATIONS

Notice of Reasons for Refusal dated Oct. 24, 2023 for corresponding Japanese Patent Application No. 2020-217397.

(Continued)

*Primary Examiner* — Thomas R Artman
(74) *Attorney, Agent, or Firm* — Muir Patent Law, PLLC

(57) ABSTRACT

An X-ray imaging apparatus is provided with an X-ray irradiation unit, an X-ray detection unit, a moving mechanism unit movable in a state of supporting the X-ray irradiation unit, an optical feature point acquisition unit, and a notification unit. The optical feature point acquisition unit is provided on either one of the X-ray irradiation unit and the X-ray detection unit and is configured to optically detect a feature point provided on the other of the X-ray irradiation unit and the X-ray detection unit to acquire the position of the feature point. The positional deviation acquisition unit acquires the positional deviation of the relative position between the X-ray irradiation unit and the X-ray detection unit based on the position of the feature point. The notification unit performs a notification based on the positional deviation.

11 Claims, 9 Drawing Sheets

(51) Int. Cl.
*A61B 6/42* (2024.01)
*A61B 6/46* (2024.01)
*A61B 6/58* (2024.01)
A61B 6/04 (2006.01)

(52) U.S. Cl.
CPC .......... *A61B 6/4405* (2013.01); *A61B 6/4452* (2013.01); *A61B 6/461* (2013.01); *A61B 6/547* (2013.01); *A61B 6/0492* (2013.01); *A61B 2560/0437* (2013.01)

(58) Field of Classification Search
CPC ....... A61B 6/4452; A61B 6/461; A61B 6/547; A61B 6/587; A61B 2560/0437
See application file for complete search history.

(56) References Cited

U.S. PATENT DOCUMENTS

| | | | | |
|---|---|---|---|---|
| 6,702,459 | B2* | 3/2004 | Barnes | A61B 6/4291 378/197 |
| 7,581,884 | B1* | 9/2009 | Barnes | A61B 6/06 378/205 |
| 7,581,885 | B2* | 9/2009 | Ertel | A61B 6/587 378/204 |
| 7,744,279 | B2* | 6/2010 | Heath | G03B 42/02 378/197 |
| 7,798,710 | B1* | 9/2010 | Barnes | A61B 6/587 378/197 |
| 8,357,904 | B2* | 1/2013 | Tsuchiya | A61B 6/037 250/363.02 |
| 8,821,015 | B2* | 9/2014 | Stagnitto | A61B 6/4291 378/205 |
| 8,827,554 | B2* | 9/2014 | Lalena | A61B 6/547 378/98.5 |
| 9,155,509 | B2 | 10/2015 | Lalena et al. | |
| 9,179,886 | B2* | 11/2015 | Stagnitto | A61B 6/08 |
| 9,693,746 | B2* | 7/2017 | Ancar | A61B 6/487 |
| 9,931,089 | B2* | 4/2018 | Nariyuki | A61B 6/107 |
| 10,136,866 | B2* | 11/2018 | Onobori | A61B 6/4452 |
| 10,517,562 | B2* | 12/2019 | Gu | A61B 6/08 |
| 10,610,171 | B2* | 4/2020 | Imamura | A61B 6/464 |
| 10,779,793 | B1* | 9/2020 | Wang | A61B 6/587 |
| 10,835,199 | B2* | 11/2020 | Chtcheprov | A61B 6/04 |
| 10,939,884 | B2* | 3/2021 | Nariyuki | A61B 6/462 |
| 11,020,068 | B2* | 6/2021 | Imamura | A61B 6/466 |
| 11,382,582 | B1* | 7/2022 | Ruff | A61B 6/5247 |
| 2002/0150215 | A1* | 10/2002 | Barnes | A61B 6/547 378/197 |
| 2006/0109958 | A1* | 5/2006 | Ertel | A61B 6/547 378/205 |
| 2008/0130837 | A1* | 6/2008 | Heath | A61B 6/587 378/205 |
| 2009/0086926 | A1* | 4/2009 | Wang | G03B 42/02 340/815.45 |
| 2011/0164728 | A1* | 7/2011 | Tsuchiya | A61B 6/4291 378/62 |
| 2011/0249793 | A1* | 10/2011 | Lalena | A61B 6/4266 378/62 |
| 2012/0230473 | A1* | 9/2012 | Stagnitto | A61B 6/4291 378/205 |
| 2014/0341349 | A1* | 11/2014 | Lalena | A61B 6/587 378/62 |
| 2015/0049863 | A1* | 2/2015 | Stagnitto | A61B 6/587 378/205 |
| 2016/0287194 | A1 | 10/2016 | Nariyuki et al. | |
| 2017/0219498 | A1* | 8/2017 | Chtcheprov | G01T 1/2978 |
| 2018/0092619 | A1* | 4/2018 | Gu | A61B 6/465 |
| 2018/0116623 | A1 | 5/2018 | Inoue et al. | |
| 2018/0146937 | A1* | 5/2018 | Nariyuki | A61B 6/4452 |
| 2018/0235558 | A1* | 8/2018 | Onobori | A61B 6/40 |
| 2019/0046130 | A1* | 2/2019 | Imamura | A61B 6/547 |
| 2020/0187876 | A1* | 6/2020 | Imamura | A61B 6/467 |
| 2020/0281556 | A1* | 9/2020 | Wang | G06T 7/74 |
| 2022/0202388 | A1* | 6/2022 | Tanaka | A61B 6/547 |
| 2023/0277148 | A1* | 9/2023 | Okumura | A61B 6/4452 378/62 |

FOREIGN PATENT DOCUMENTS

JP 2016193177 A 11/2016
WO 2016208155 A1 12/2016

OTHER PUBLICATIONS

First Office Action dated Mar. 29, 2025 for corresponding Chinese Patent Application No. 202111411389.5.

\* cited by examiner

First modification

First modification

Second modification

Third modification

X-RAY IMAGING APPARATUS AND POSITIONAL DEVIATION DETECTION UNIT FOR X-RAY IMAGING APPARATUS

CROSS-REFERENCE TO RELATED APPLICATIONS

The priority application number JP2020-217397, entitled "X-ray imaging apparatus and positional deviation detection unit for X-ray imaging apparatus", filed on Dec. 25, 2020, invented by TANAKA Masato, HIBI Masahiro, KINOSHITA Hiroyuki, upon which this patent application is based, is hereby incorporated by reference.

BACKGROUND OF THE INVENTION

Field of the Invention

The present invention relates to an X-ray imaging apparatus and a positional deviation detection unit for an X-ray imaging apparatus. In particular, the present invention relates to an X-ray imaging apparatus and a positional deviation detection unit for an X-ray imaging apparatus that detects a positional deviation of a relative position between an X-ray irradiation unit and an X-ray detection unit.

Description of the Background Art

Conventionally, an X-ray imaging apparatus and a positional deviation detection unit for an X-ray imaging apparatus that detects a positional deviation of a relative position between an X-ray irradiation unit and an X-ray detection unit are known. Such X-ray imaging apparatus and positional deviation detection unit for an X-ray imaging apparatus are disclosed, for example, in Japanese Translation of PCT International Application Publication No. 2013-523396.

A radiation photographing apparatus disclosed in Japanese Translation of PCT International Application Publication No. 2013-523396 is provided with a radiation source, an image receiver, a collimator, and a display device. The collimator disclosed in Japanese Translation of PCT International Application Publication No. 2013-523396 is provided with a sensor element. Further, Japanese Translation of PCT International Application Publication No. 2013-523396 discloses a configuration provided with a holder for holding an image receiver. The holder holds an electromagnetic coil together with the image receiver. Japanese Translation of PCT International Application Publication No. 2013-523396 discloses a configuration for detecting a positional deviation between a radiation source and an image receiver. The positional deviation between the radiation source and the receiver is detected by detecting the electromagnetic wave emitted from the electromagnetic coil held in the holder by the sensor element provided in the collimator.

However, as disclosed in Japanese Translation of PCT International Application Publication No. 2013-523396, the configuration in which the electromagnetic wave emitted from the electromagnetic coil is detected by the sensor element has the following disadvantages. That is, due to the electromagnetic wave emitted from an electron device placed in the vicinity of the radiation photography apparatus (X-ray imaging apparatus), the detection accuracy of the electromagnetic wave by the sensor device deteriorates. The deterioration of the detection accuracy of the electromagnetic wave by the sensor element causes a problem that the detection accuracy of the positional deviation between the radiation source (X-ray irradiation unit) and the receiver (X-ray detection unit) deteriorates.

SUMMARY OF THE INVENTION

The present invention has been made to solve the above-described problems. One object of the present invention is to provide an X-ray imaging apparatus and a positional deviation detection unit for an X-ray imaging apparatus capable of suppressing deterioration of detection accuracy of a positional deviation between an X-ray irradiation unit and an X-ray detection unit due to an electron device placed in the vicinity of the X-ray imaging apparatus and the positional deviation detection unit.

Means for Solving the Problem

In order to attain the above-described object, an X-ray imaging apparatus according to a first aspect of the present invention, is provided with:
an X-ray irradiation unit configured to emit X-rays to a subject;
an X-ray detection unit to be placed at the time of X-ray irradiation, the X-ray detection unit being configured to detect the X-rays emitted from the X-ray irradiation unit;
a moving mechanism unit configured to be movable in a state of supporting the X-ray irradiation unit;
an optical feature point acquisition unit provided on either one of the X-ray irradiation unit and the X-ray detection unit, the optical feature point acquisition unit being configured to optically detect a feature point provided on the other of the X-ray irradiation unit and the X-ray detection unit to acquire a position of the feature point;
a positional deviation acquisition unit configured to acquire a positional deviation of a relative position between the X-ray irradiation unit and the X-ray detection unit, based on the position of the feature point acquired by the optical feature point acquisition unit; and
a notification unit configured to perform a notification based on the positional deviation acquired by the positional deviation acquisition unit.

Further, in order to attain the above-described object, a positional deviation detection unit for an X-ray imaging apparatus according to a second aspect of the present invention, the X-ray imaging apparatus being composed of an X-ray irradiation unit for irradiating a subject with X-rays, an X-ray detection unit to be arranged at the time of X-ray irradiation to detect the X-rays emitted from the X-ray irradiation unit, and a moving mechanism unit configured to be movable in a state of supporting the X-ray irradiation unit, the positional deviation detection unit is provided with:
an optical feature point acquisition unit provided on either one of the X-ray irradiation unit and the X-ray detection unit, the optical feature point acquisition unit being configured to optically detect a feature point provided on the other of the X-ray irradiation unit and the X-ray detection unit to acquire a position of the feature point;
a positional deviation acquisition unit configured to acquire a positional deviation of a relative position between the X-ray irradiation unit and the X-ray detection unit, based on the position of the feature point acquired by the optical feature point acquisition unit; and a notification unit configured to perform a notification based on the positional deviation acquired by the positional deviation acquisition unit.

In the X-ray imaging apparatus according to the above-described first aspect of the present invention, as described above, the X-ray imaging apparatus is provided with the optical feature point acquisition unit for acquiring the position of the feature point by optically detecting the feature point, a positional deviation acquisition unit for acquiring the positional deviation of the relative position between the X-ray irradiation unit and the X-ray detection unit, and a notification unit for performing a notification based on the positional deviation.

This allows the optical feature point acquisition unit to optically acquire the position of the feature point. Therefore, even if an electromagnetic wave is emitted from another electron device placed in the vicinity of the X-ray imaging apparatus, the position of the feature point can be accurately acquired by the optical feature point acquisition unit. Therefore, it is possible to suppress the deterioration of the accuracy of acquiring the position of the feature point due to the electromagnetic wave emitted from another electron device. Consequently, it is possible to provide an X-ray imaging apparatus that can suppress the deterioration of the detection accuracy of the positional deviation between the X-ray irradiation unit and the X-ray detection unit due to the electron device placed in the vicinity of the X-ray imaging apparatus.

Further, the positional deviation detection unit for an X-ray imaging apparatus according to the above-described second aspect of the present invention is provided with the optical feature point acquisition unit for acquiring the position of the feature point by optically detecting the feature point, the positional deviation acquisition unit for acquiring the position of the relative position between the X-ray irradiation unit and the X-ray detection unit, and the notification unit for performing a notification based on the positional deviation.

With this, in the same manner as in the X-ray imaging apparatus according to the above-described first aspect of the present invention, it is possible to provide a positional deviation detection unit for an X-ray imaging apparatus capable of suppressing the deterioration of the detection accuracy of the positional deviation between the X-ray irradiation unit and the X-ray detection unit due to an electron device placed in the vicinity of the positional deviation detection unit,

DESCRIPTION OF THE PREFERRED EMBODIMENT (Configuration of X-ray Imaging Apparatus)

Figure 1:
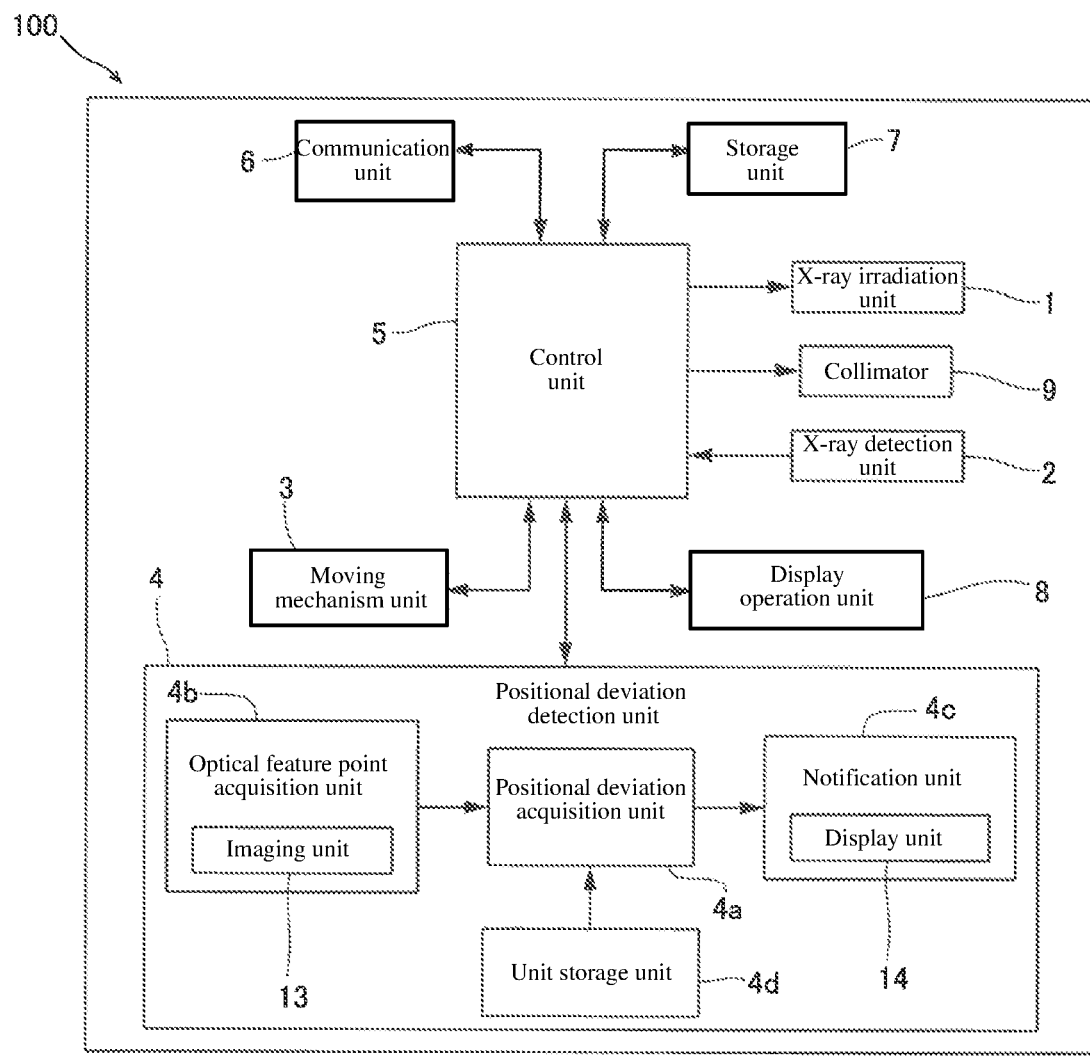
FIG. 1 is a block diagram showing an entire configuration of an X-ray imaging apparatus according to one embodiment of the present invention.

Referring to FIG. 1, a configuration of an X-ray imaging apparatus 100 according to one embodiment will be described.

As shown in FIG. 1, the X-ray imaging apparatus 100 according to this embodiment is provided with an X-ray irradiation unit 1, an X-ray detection unit 2, a moving mechanism unit 3, a positional deviation detection unit 4, a control unit 5, a communication unit 6, a storage unit 7, a display operation unit 8, and a collimator 9. Note that the positional deviation detection unit 4 is an example of the "positional deviation detection unit for an X-ray imaging apparatus" recited in claims.

Figure 3:
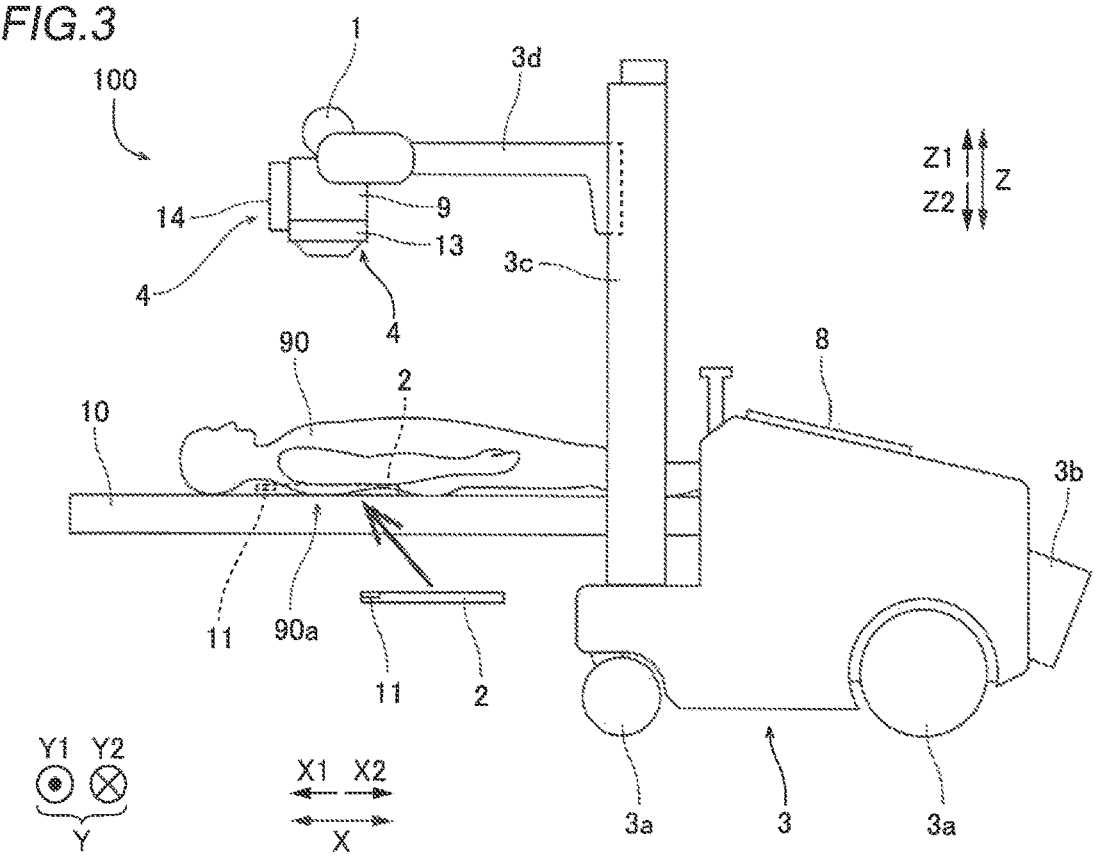
FIG. 3 is a side view showing a state at the time of imaging by an X-ray imaging apparatus according to one embodiment.

The X-ray irradiation unit 1 is configured to emit X-rays onto a subject 90 (see FIG. 3). The X-ray irradiation unit 1 is configured to emit X-rays when a voltage is applied by an X-ray tube drive unit (not shown).

The X-ray detection unit 2 is placed at the time of X-ray irradiation to detect X-rays emitted from the X-ray irradiation unit 1. The X-ray detection unit 2 includes, for example, an FPD (flat panel detector). Further, in this embodiment, the X-ray detection unit 2 is configured as a wireless-type X-ray detector and can be carried separately from the X-ray imaging apparatus 100. The X-ray detection unit 2 is configured to be accommodated in a storage portion 3b (see FIG. 2) to be described later, other than when performing X-ray imaging.

The moving mechanism unit 3 is configured to be movable in a state of supporting the X-ray irradiation unit 1. The detailed configuration of the moving mechanism unit 3 will be described later.

The positional deviation detection unit 4 is used for an X-ray imaging apparatus 100 provided with the X-ray irradiation unit 1, the X-ray detection unit 2, and the moving mechanism unit 3. The positional deviation detection unit 4 is configured to detect the positional deviation between the X-ray irradiation unit 1 and the X-ray detection unit 2 and notify the detected positional deviation. In this embodiment, as shown in FIG. 1, the positional deviation detection unit 4 is provided with a positional deviation acquisition unit 4a, an optical feature point acquisition unit 4b, a notification unit 4c, and a unit storage unit 4d.

The positional deviation acquisition unit 4a is configured to acquire the positional deviation of the relative position between the X-ray irradiation unit 1 and the X-ray detection unit 2, based on the position of the feature point 11 (see FIG. 3) acquired by the optical feature point acquisition unit 4b. The positional deviation acquisition unit 4a is, for example, a computer configured to include a CPU (Central Processing Unit), a ROM (Read Only Memory), a RAM (Random Access Memory), and the like. The configuration in which the positional deviation acquisition unit 4a acquires the positional deviation between the X-ray irradiation unit 1 and the X-ray detection unit 2 will be described later.

The optical feature point acquisition unit 4b is provided on either one of the X-ray irradiation unit 1 and the X-ray detection unit 2. The optical feature point acquisition unit 4b is configured to acquire the position of the feature point 11 (see FIG. 3) by optically detecting the feature point 11 provided on the other of the X-ray irradiation unit 1 and the X-ray detection unit 2. In this embodiment, the optical feature point acquisition unit 4b includes an imaging unit 13 for acquiring the position information on the feature point 11 by imaging the feature point 11. The imaging unit 13 includes, for example, a CCD (Charge Coupled Device) sensor or a CMOS (Complementary Metal Oxide Semiconductor) sensor. The configuration in which the optical feature point acquisition unit 4b (imaging unit 13) acquires the position of the feature point 11 will be described later.

The notification unit 4c is configured to perform a notification based on the positional deviation acquired by the positional deviation acquisition unit 4a. In this embodiment, the notification unit 4c includes a display unit 14 that displays a positional deviation along with an image 20 of a subject 90 (see FIG. 8) captured by the imaging unit 13. The display unit 14 includes, for example, a liquid crystal monitor.

The unit storage unit 4d is provided with a non-volatile memory. In the unit storage unit 4d, the distance 60 (FIG. 6) in which the X-ray irradiation unit 1 and the imaging unit 13 are spaced apart from each other has been stored.

The control unit 5 is a computer configured to include a CPU, a ROM, a RAM, and the like. The control unit 5 is configured so as to display the captured X-ray image on the display operation unit 8. Further, the control unit 5 is configured to perform control of various configurations of the X-ray imaging apparatus 100, based on the operation input by the display operation unit 8.

The communication unit 6 is configured to be able to communicate with an external networking. The communication unit 6 is configured to be able to acquire imaging order information on the subject 90 from the outside and transmit the captured X-ray image to the outside. Note that the imaging order information is input in advance by, for example, an external server (not shown) and transmitted from the outside to the X-ray imaging apparatus 100. The X-ray imaging is performed based on the imaging order information by the radiation technician traveling or waiting in a hospital with the X-ray imaging apparatus 100.

The storage unit 7 includes, for example, a non-volatile memory. Programs used for processing the control unit 5 are stored in the storage unit 7. Further, the storage unit 7 is configured to be able to store the imaging order information acquired by the communication unit 6, the captured X-ray image, and the like.

The display operation unit 8 is configured, for example, as a touch panel type liquid crystal display. The display operation unit 8 functions as a display unit on which an X-ray image and an imaging order information, and the like, are displayed, and functions as an input unit to which various operations are input.

(Apparatus Configuration)

Figure 2:
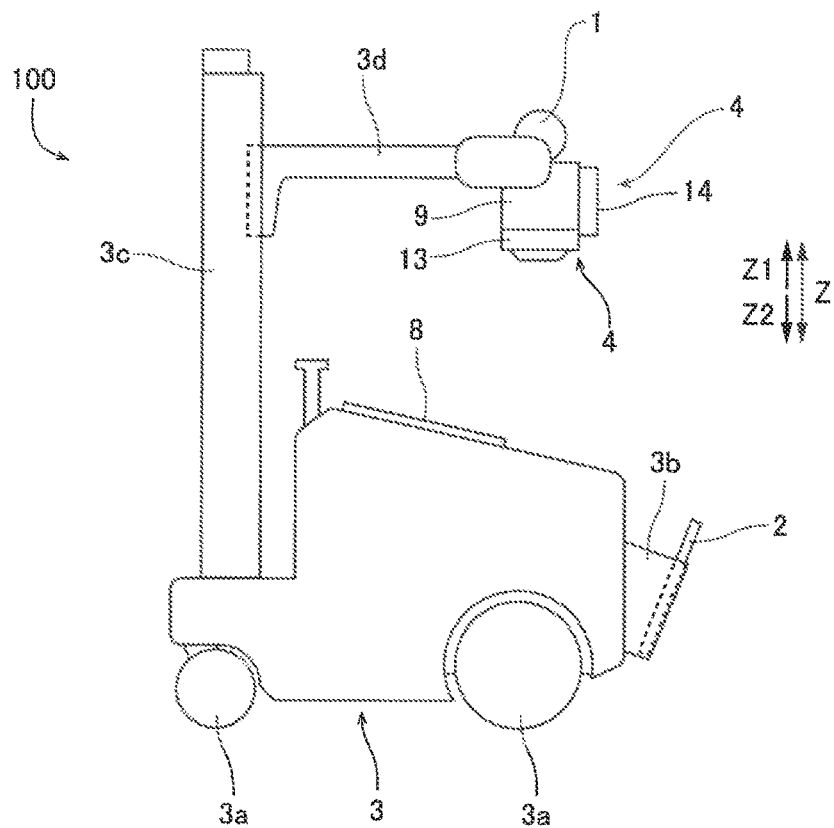
FIG. 2 is a side view showing an entire configuration of an X-ray imaging apparatus according to one embodiment.

As shown in FIG. 2, the X-ray imaging apparatus 100 according to this embodiment is configured such that the entire apparatus can be moved to perform X-ray imaging by moving to the patient (subject 90, see FIG. 3) in each hospital room of a hospital at the time of doctor's rounds. In the X-ray imaging apparatus 100, the X-ray irradiation unit 1, the X-ray detection unit 2, and the display operation unit 8 are provided on the moving mechanism unit 3. Further, the positional deviation detection unit 4 and the collimator 9 are provided on the X-ray irradiation unit 1. Note that in this embodiment, the up-down direction is defined as a Z-direction. In the Z-direction, the upward direction is defined as a Z1-direction, and the downward direction is defined as a Z2-direction.

The moving mechanism unit 3 is configured as a carriage of the X-ray imaging apparatus 100. A power supply device (not shown), a battery (not shown), or the like are provided therein. Further, the moving mechanism unit 3 is provided with a plurality of wheels 3a, a storage portion 3b, a support 3c, and an arm portion 3d.

A plurality of wheels 3a is provided at the lower portion of the moving mechanism unit 3. With this, the X-ray imaging apparatus 100 can be moved.

Further, the storage portion 3b is provided at the rear of the moving mechanism unit 3. The storage portion 3b is configured to store the X-ray detection unit 2 such that the X-ray detection unit 2 can be taken out.

Further, the moving mechanism unit 3 is provided with the support 3c.

Specifically, the support 3c is mounted at the front of the moving mechanism unit 3 so as to extend in a vertical direction. The inside of the support 3c is hollowed, and the components for causing the arm portion 3d to be raised and lowered are housed inside. That is, the X-ray irradiation unit 1 and the collimator 9 are provided so that they can be raised and lowered in accordance with the raising and lowering motion of the arm portion 3d. Further, the support 3c is configured to be rotatable in a horizontal direction.

The arm portion 3d is mounted so as to extend from the support 3c in a horizontal direction. Further, the arm portion 3d can be moved upward and downward with respect to the support 3c and can be extended and contracted to change the horizontal position of the X-ray irradiation unit 1.

As shown in FIG. 3, when imaging the subject 90, the X-ray irradiation unit 1 is placed in front of the support 3c (in the X1-direction) from the state in which it is positioned behind (in the X-2 direction) the support 3c shown in FIG. 2. Further, the X-ray detection unit 2 is placed between the subject 90 and the top board 10 on which the subject 90 is placed at the time of the X-ray irradiation. That is, at the time of the X-ray irradiation (at the time of imaging the subject 90), the X-ray detection unit 2 is placed on the side of the subject 90 placed on the top board 10 opposite to the X-ray irradiation unit 1 (i.e., at the position shown by the dotted line on the back 90a side of the subject 90), by a person (radiation technician) who performs the X-ray imaging.

Note that in this embodiment, the longitudinal direction of the top board 10 is defined as an X-direction. The direction on the side of the subject 90 on which the head is arranged is defined as an X1-direction, and the direction on the side of the subject 90 on which the foot is arranged is defined as an X2-direction. The transverse direction (left-right direction of the subject 90) of the top board 10 perpendicular to the X-direction is defined as Y-direction. The direction of the right-hand side of the subject 90 when the subject 90 lies on the back is defined as a Y1-direction, and the direction of the left-hand side is defined as the Y2-direction. Note that the top board 10 denotes a top board of a bed used by the subject 90 in a hospital room.

Here, the X-ray irradiation unit 1 is configured to be freely movable by a doctor, a radiation technician, or the like. The X-ray detection unit 2 is placed by a radiation technician or the like. Therefore, the positional deviation may occur in the relative position between the X-ray irradiation unit 1 and the X-ray detection unit 2. When there is a positional deviation between the X-ray irradiation unit 1 and the X-ray detection unit 2, there is a possibility that the imaging site cannot be imaged accurately.

The positional deviation between the X-ray irradiation unit 1 and the X-ray detection unit 2 denotes that the optical axis 1a (see FIG. 6) of the X-rays emitted from the X-ray irradiation unit 1 and the center 2c (see FIG. 5) of the X-ray detection unit 2 are shifted in position. Further, the angular deviation between the X-ray irradiation unit 1 and the X-ray detection unit 2 includes the deviation in the rotation direction in the plane (in the LM-plane) of the X-ray detection unit 2.

Therefore, in this embodiment, it is configured such that the positional deviation detection unit 4 acquires the positional deviation between the X-ray irradiation unit 1 and the X-ray detection unit 2 and performs a notification of the positional deviation by the display unit 14.

(Arrangement of Imaging Unit, Feature Point, and Display Unit)

In this embodiment, as shown in FIG. 3, the imaging unit 13 is provided at the X-ray irradiation unit 1. In this embodiment, the imaging unit 13 is configured to image the subject 90 by visible light. Specifically, the imaging unit 13 is configured to capture the color moving image by visible light.

Further, in this embodiment, as shown in FIG. 3, the feature point 11 is provided on the X-ray detection unit 2.

Further, in this embodiment, as shown in FIG. 3, the display unit 14 is provided at the X-ray irradiation unit 1 in a position different from the position of the imaging unit 13.

In this embodiment, the optical feature point acquisition unit 4b (imaging unit 13) and the display unit 14 are provided so as to be mountable to the X-ray irradiation unit 1. The imaging unit 13 and the display unit 14 are configured to be attached to the X-ray irradiation unit 1 later. In the example shown in FIG. 3, the imaging unit 13 is provided on the Y1-direction side surface of the X-ray irradiation unit 1. Further, the display unit 14 is provided on the X1-direction side surface of the X-ray irradiation unit 1. That is, the positional deviation detection unit 4 is configured to be mountable with respect to the X-ray irradiation unit 1. In other words, the positional deviation detection unit 4 is configured to be retrofitted with respect to the X-ray irradiation unit 1.

(Feature Point Arrangement)

Figure 4:
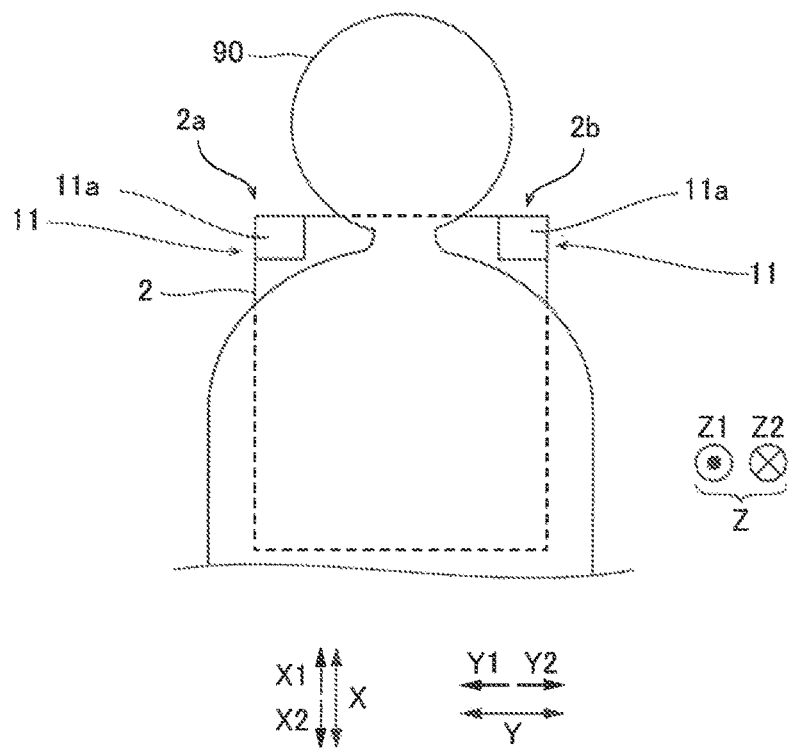
FIG. 4 is a schematic diagram for explaining a feature point provided on an X-ray detection unit according to one embodiment.

As shown in FIG. 4, the feature point 11 includes a marker member 11a. The marker member 11a is provided on the X-ray detection unit 2. The marker member 11a is provided separately from the X-ray detection unit 2 and is provided on the X-ray detection unit by being adhered thereto. The details of the marker member 11a will be described later. In this embodiment, the feature point 11 (marker member 11a) is provided at the corner 2a of the X-ray detection unit 2. Specifically, the feature point 11 is provided on the surface of the X-ray detection unit 2 on which the subject 90 is placed. Note that in this embodiment, the feature point 11 (marker member 11a) is provided also at the corner 2b of the X-ray detection unit 2.

(Planar Marker)

Figure 5:
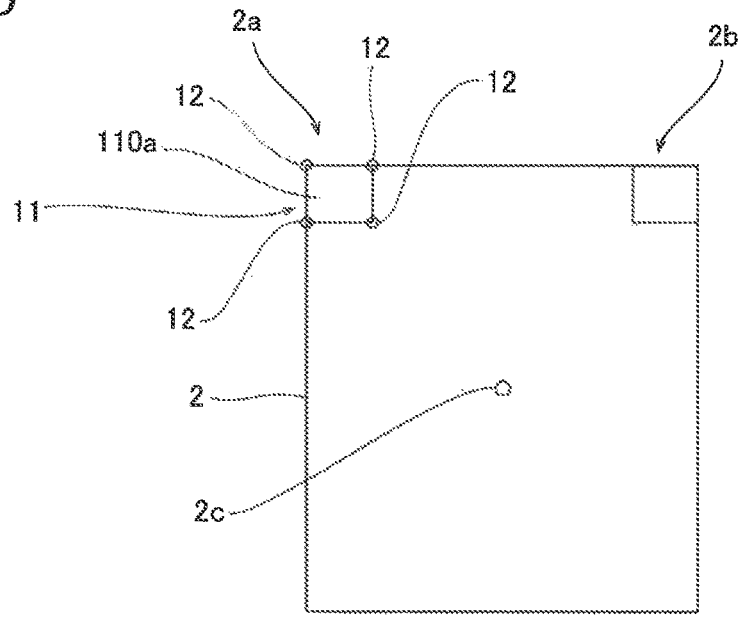
FIG. 5 is a schematic diagram for explaining a configuration in which a positional deviation acquisition unit according to one embodiment acquires a positional deviation between an X-ray irradiation unit and an X-ray detection unit based on a feature point.

In this embodiment, as shown in FIG. 5, the feature point 11 includes a planar marker 110a. The X-ray detection unit 2 is provided with at least one planar marker 110a. In the embodiment shown in FIG. 5, two planar markers 110a are provided at two positions, i.e., the corner 2a and the corner 2b, of the X-ray detection unit 2. The planar marker 110a includes at least either one of a printed figure and an outline of the X-ray detection unit 2. In this embodiment, the planar marker 110a is a printed figure. Specifically, the planar marker 110a is a figure printed on one side surface of a pressure-sensitive adhesive sheet provided with a pressure-sensitive adhesive on the other side surface. As shown in FIG. 5, the planar marker 110a is a rectangular shaped figure. In the planar marker 110a, information capable of being acquired by capturing an image with a camera or the like is set in advance. The planar marker 110a is a so-called AR marker.

The planar marker 110a includes three or more recognition points 12 to be recognized by the imaging unit 13. In the example shown in FIG. 5, the planar marker 110a includes four recognition points 12. In the example shown in FIG. 5, each corner of the planar marker 110a serves as a recognition point 12. In this embodiment, the long side direction of the X-ray detection unit 2 is defined as an L-direction, and the short side direction of the X-ray detection unit 2 is defined as an M-direction.

(Acquisition of Positional Deviation Between X-Ray Irradiation Unit and X-Ray Detection Unit)

In this embodiment, the positional deviation acquisition unit 4a is configured to acquire the positional deviation between the center 30a (see FIG. 8) of the irradiation range of the X-rays emitted from the X-ray irradiation unit 1 and the center 2c of the X-ray detection unit 2 as a positional deviation between the X-ray irradiation unit 1 and the X-ray detection unit 2. Specifically, the positional deviation acquisition unit 4a acquires the center 30a of the irradiation range of the X-rays in the coordinate system (hereinafter referred to as "image coordinate system") of the image 20 of the subject 90 and the center 2c of the X-ray detection unit 2 in the image coordinate system. With this, the positional deviation acquisition unit 4a acquires the positional deviation between the X-ray irradiation unit 1 and the X-ray detection unit 2.

Figure 6:
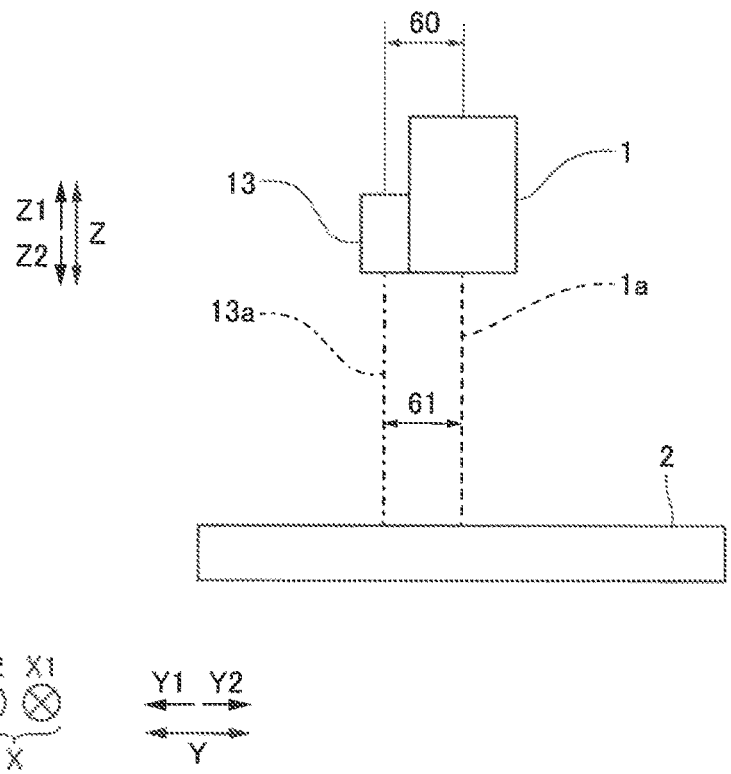
FIG. 6 is a schematic diagram for explaining a configuration in which a positional deviation acquisition unit according to one embodiment acquires a position of a center of an X-ray irradiation unit.

Here, as shown in FIG. 6, the imaging unit 13 is located at a position spaced apart by a predetermined distance 60 from the X-ray irradiation unit 1. That is, the distance 61 between the optical axis 1a of the X-rays emitted from the X-ray irradiation unit 1 to the X-ray detection unit 2 and the imaging center 13a of the imaging unit 13 is equal to the distance 60 by which the X-ray irradiation unit 1 and the imaging unit 13 are separated from each other. Therefore, the position of the center 30a of the irradiation range of the X-rays in the image coordinate system can be acquired based on the distance 60 by which the imaging center 13a and the optical axis 1a of the X-rays are separated from each other. Therefore, when it is possible to acquire the position of the center 2c of the X-ray detection unit 2 at the time of the X-ray irradiation (at the time of imaging) in the image coordinate system, the positional deviation acquisition unit 4a can acquire the positional deviation between the X-ray irradiation unit 1 and the X-ray detection unit 2. Note that the distance 60 by which the X-ray irradiation unit 1 and imaging unit 13 are spaced apart is acquired in advance and has been stored in the unit storage unit 4d (see FIG. 1).

Figure 7:
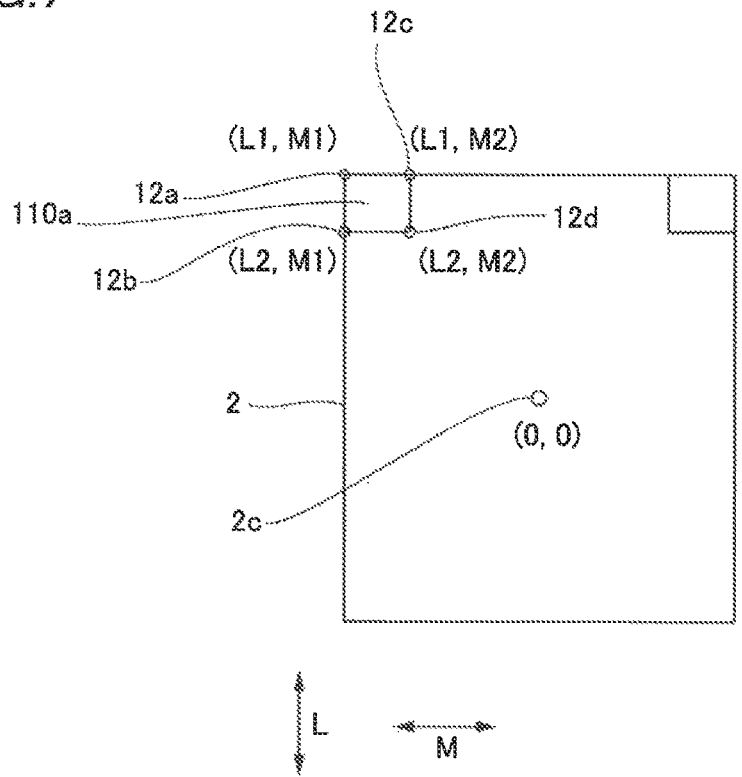
FIG. 7 is a schematic diagram for explaining a configuration in which a positional deviation acquisition unit according to one embodiment acquires a position of a center of an X-ray detection unit.

In this embodiment, as shown in FIG. 7, the positional deviation acquisition unit 4a is configured to acquire the positional deviation between the X-ray irradiation unit 1 and the X-ray detection unit 2, based on the position information on the feature point 11 (planar marker 110a). Specifically, the positional deviation acquisition unit 4a is configured to acquire the position coordinate of each recognition point 12 of the planar marker 110a in the coordinate system (hereinafter referred to as an "LM coordinate system") in the plane (in the LM plane) of the X-ray detection unit 2. Further, the positional deviation acquisition unit 4a is configured to acquire the position information on the planar marker 110a in the image 20 by converting the position coordinate of the planar marker 110a in the acquired LM coordinate system into the image coordinate system.

Note that a position coordinate in the LM coordinate system is previously set to each recognition point 12 of the planar marker 110a. Specifically, a position coordinate when the coordinate of the center 2c of X-ray detection unit 2 is set to the origin is set to each recognition point 12 (each of the first recognition point 12a to the fourth recognition point 12d) of the planar marker 110a. Note that the position coordinate in the LM coordinate system includes the coordinate in the L-direction and the coordinate in the M-direction.

As shown in FIG. 7, to the first recognition point 12a, the coordinate (L1, M1) is set as a position coordinate in the LM coordinate system. Further, to the second recognition point 12b, the coordinate (L2, M1) is set as a position coordinate in the LM coordinate system. Further, to the third recognition point 12c, the coordinate (L1, M2) is set as a position coordinate in the LM coordinate system. Further, to the fourth recognition point 12d, the coordinate (L2, M2) is set as a position coordinate in the LM coordinate system. Note that to the center 2c of the X-ray detection unit 2, the coordinate (0, 0) is set as a position coordinate in the LM coordinate system.

The positional deviation acquisition unit 4a acquires the position coordinate of each recognition point 12 of the planar marker 110a in the LM coordinate system from the image 20 (see FIG. 8) captured by the imaging unit 13. The planar marker 110a includes at least three (four in this embodiment) recognition points 12. Therefore, the positional deviation acquisition unit 4a can geometrically acquire the position coordinate of the center 2c of the X-ray detection unit 2 in the LM coordinate system from the recognition point 12 of the position coordinate.

Here, the first recognition point 12a and the second recognition point 12b differ in the value of the L coordinate in the LM coordinate system and are equal in the value of the M coordinate. Further, the first recognition point 12a and the third recognition point 12c are the same in the L coordinate.

Therefore, when converting the positional coordinate of the center 2c of the X-ray detection unit 2 in the LM coordinate system into the image coordinate system, it can be performed as follows. That is, based on the coordinate value of each recognition point 12, the long side direction and the short side direction of the X-ray detection unit 2 in the LM coordinate system can be converted into the long side direction and the short side direction of the X-ray detection unit 2 in the image coordinate system. Thus, the positional deviation acquisition unit 4a can acquire the position (position coordinate) of the center 30a of the irradiation range of the X-rays in the picture coordinate system and the position (position coordinate) of the center 2c of to X-ray detection unit 2. Therefore, the positional deviation acquisition unit 4a can acquire the positional deviation between the X-ray irradiation unit 1 and the X-ray detection unit 2.

In this embodiment, the positional deviation acquisition unit 4a is configured to acquire the angular deviation based on the position information on the feature point 11 (planar marker 110a). That is, in this embodiment, the positional deviation acquisition unit 4a is configured to acquire the positional deviations in the vertical direction and in the horizontal direction in the image coordinate system and the positional deviation in the rotation direction in the plane in the image coordinate system.

(Notification of Positional Deviation)

Figure 8:
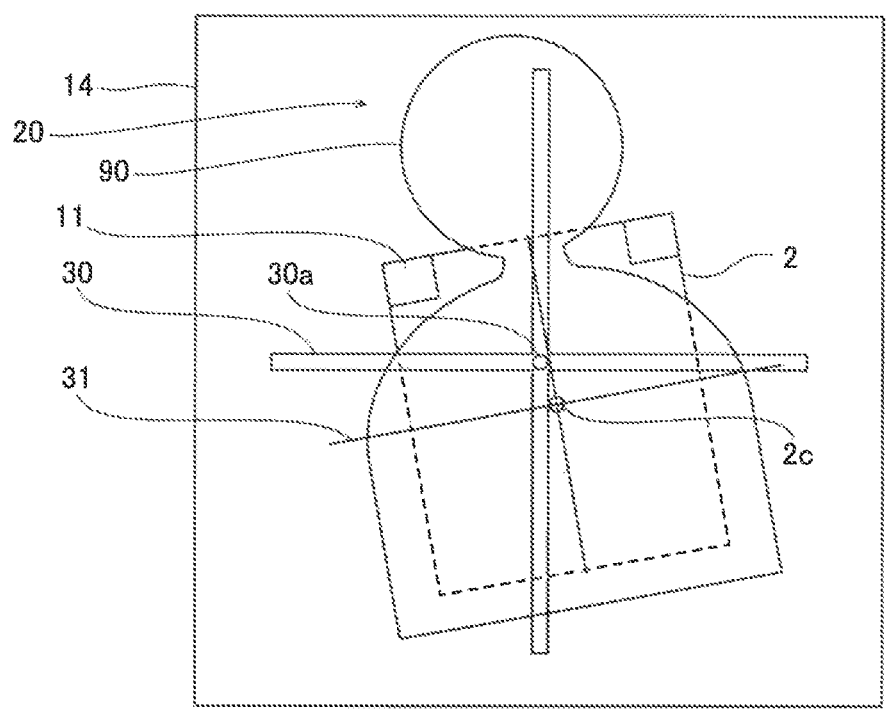
FIG. 8 is a schematic diagram for explaining an axis indicating a center of an irradiation range of X-rays displayed on a display unit and an axis indicating a center of an X-ray detection unit, according to one embodiment.

As shown in FIG. 8, in this embodiment, the display unit 14 is configured to display the positional deviation between the X-ray irradiation unit 1 and the X-ray detection unit 2 together with the image 20 of the subject 90. Specifically, the display unit 14 displays the axis 30 indicating the center 30a of the irradiation range of the X-rays emitted from the X-ray irradiation unit 1 and the axis 31 indicating the center 2c of the X-ray detection unit 2, together with the image 20 of the subject 90. With this, the positional deviation and the angular deviation between the X-ray irradiation unit 1 and the X-ray detection unit 2 can be displayed.

In the example shown in FIG. 8, the positional deviation between the X-ray irradiation unit 1 and the X-ray detection unit 2 is expressed by the deviation between the center 30a of the X-ray irradiation range and the center 2c of the X-ray detection unit 2. In the examples shown in FIG. 8, the angular deviation between the X-ray irradiation unit 1 and the X-ray detection unit 2 is expressed by the angular deviation between the axis 30 and the axis 31. Note that the angular deviation shown in FIG. 8 is an angular deviation between the X-ray irradiation unit 1 and the X-ray detection unit 2 in the image coordinate system (in the plane of the image 20).

(Positional Deviation Acquisition Processing)

Figure 9:
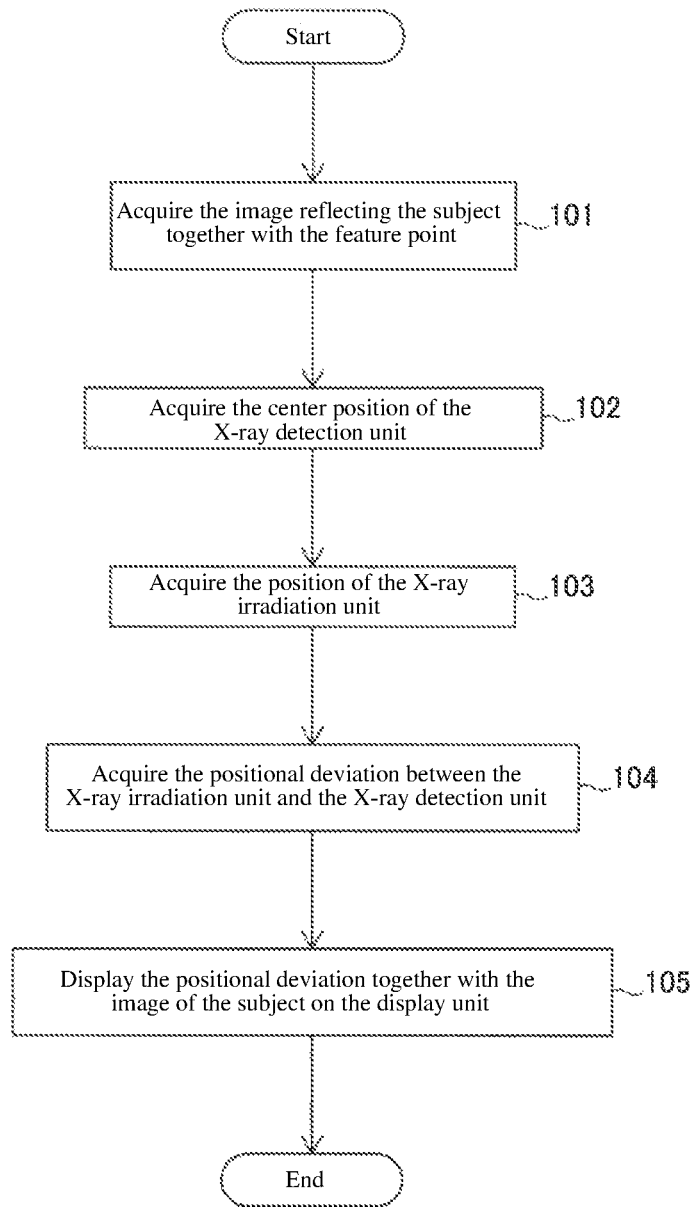
FIG. 9 is a flowchart for explaining processing in which a positional deviation acquisition unit according to one embodiment acquires a positional deviation between an X-ray irradiation unit and an X-ray detection unit.

Next, referring to FIG. 9, the processing will be described in which the positional deviation detection unit 4 acquires the positional deviation between the X-ray irradiation unit 1 and the X-ray detection unit 2.

In Step 101, the imaging unit 13 acquires the image 20 of the subject 90. Specifically, the imaging unit 13 acquires the image 20 in which the subject 90 is reflected together with the feature point 11.

In Step 102, the positional deviation acquisition unit 4a acquires the position of the center 2c of the X-ray detection unit 2 based on the image 20. Specifically, the positional deviation acquisition unit 4a acquires the position information on the center 2c of the X-ray detection unit 2, based on the position information on the recognition point 12 of the planar marker 110a.

In Step 103, the positional deviation acquisition unit 4a acquires the position information on the X-ray irradiation unit 1. Specifically, the positional deviation acquisition unit 4a acquires the position coordinate of the center 30a of the irradiation range of the X-rays from the unit storage unit 4d (see FIG. 1), as the position information on the X-ray irradiation unit 1.

In Step 104, the positional deviation acquisition unit 4a acquires the positional deviation between the X-ray irradiation unit 1 and the X-ray detection unit 2, based on the position information on the center 2c of the X-ray detection unit 2 and the position information on the X-ray irradiation unit 1.

In Step 105, the positional deviation acquisition unit 4a makes the display unit 14 display the acquired positional deviation between the X-ray irradiation unit 1 and the X-ray detection unit 2, together with the image 20 of the subject 90, on the display unit 14. Thereafter, the processing ends.

Note that the processing of Step 101 and Step 102 and the processing of Step 103 may be performed first.

In this embodiment, in the display unit 14, the positional deviation between the X-ray irradiation unit 1 and the X-ray detection unit 2 is displayed. Therefore, a doctor, a radiation technician, or the like can perform the alignment between the X-ray irradiation unit 1 and the X-ray detection unit 2 while checking the display unit 14. Specifically, a doctor or the like moves the X-ray irradiation unit 1 such that the center 30a of the irradiation range of the X-rays in the image 20 and the center 2c of the X-ray detection unit 2 overlap with each other. Further, a doctor or the like moves the X-ray irradiation unit 1 such that the axis 30 and the axis 31 overlap with each other. This completes the alignment between the X-ray irradiation unit 1 and the X-ray detection unit 2.

Effects of this Embodiment

In this embodiment, the following effects can be obtained.

In this embodiment, as described above, the X-ray imaging apparatus 100 is provided with the X-ray irradiation unit 1, the X-ray detection unit 2, the moving mechanism unit 3, the optical feature point acquisition unit 4b, the positional deviation acquisition unit 4a, and the notification unit 4c. The X-ray irradiation unit 1 irradiates the subject 90 with X-rays. The X-ray detection unit 2 is placed at the time of X-ray irradiation and detects the X-rays emitted from the X-ray irradiation unit 1. The moving mechanism unit 3 is movable in a state of supporting the X-ray irradiation unit 1. The optical feature point acquisition unit 4b is provided on either one of the X-ray irradiation unit 1 and the X-ray detection unit 2. The optical feature point acquisition unit 4b acquires the position of the feature point 11 by optically detecting the feature point 11 provided on the other of the X-ray irradiation unit 1 and the X-ray detection unit 2. The positional deviation acquisition unit 4a acquires the positional deviation of the relative position between the X-ray irradiation unit 1 and the X-ray detection unit 2, based on the position of the feature point 11 acquired by the optical feature point acquisition unit 4b. The notification unit 4c performs a notification based on the positional deviation acquired by the positional deviation acquisition unit 4a.

Thus, the optical feature point acquisition unit 4b optically acquires the position of the feature point 11. Therefore, even if an electromagnetic wave is emitted from another electron device placed in the vicinity of the X-ray imaging apparatus 100, it is possible to accurately acquire the position of the feature point 11 by the optical feature point acquisition unit 4b. Therefore, it is possible to suppress the deterioration of the accuracy of acquiring position of the feature point 11 due to an electromagnetic wave emitted from other electron devices. Consequently, it is possible to provide an X-ray imaging apparatus 100 capable of suppressing deterioration of the detection accuracy of the positional deviation between the X-ray irradiation unit 1 and the X-ray detection unit 2 due to an electron device placed in the vicinity of the X-ray imaging apparatus 100.

Further, in this embodiment, as described above, the positional deviation detection unit (positional deviation detection unit 4) for an X-ray imaging apparatus is used in the X-ray imaging apparatus 100 provided with the X-ray irradiation unit 1, the X-ray detection unit 2, and the moving mechanism unit 3. The X-ray irradiation unit 1 irradiates the subject 90 with X-rays. The X-ray detection unit 2 is arranged at the time of X-ray irradiation and detects the X-rays emitted from the X-ray irradiation unit 1. The moving mechanism unit 3 is movable in a state of supporting the X-ray irradiation unit 1.

This positional deviation detection unit for an X-ray imaging apparatus is provided with the optical feature point acquisition unit 4b, the positional deviation acquisition unit 4a, and the notification unit 4c. The optical feature point acquisition unit 4b is provided on either one of the X-ray irradiation unit 1 and the X-ray detection unit 2 to acquire the position of the feature point 11 by optically detecting the feature point 11 provided on the other of the X-ray irradiation unit 1 and the X-ray detection unit 2. The positional deviation acquisition unit 4a acquires the positional deviation of the relative position between the X-ray irradiation unit 1 and the X-ray detection unit 2, based on the position of the feature point 11 acquired by the optical feature point acquisition unit 4b. The notification unit 4c performs a notification based on the positional deviation acquired by the positional deviation acquisition unit 4a.

Thus, in the same manner as in the above-described X-ray imaging apparatus 100, it is possible to provide a positional deviation detection unit (positional deviation detection unit 4) for an X-ray imaging apparatus. That is, it is possible to provide a positional deviation detection unit (positional deviation detection unit 4) for an X-ray imaging apparatus capable of suppressing deterioration of the detection accuracy of the positional deviation between the X-ray irradiation unit 1 and the X-ray detection unit 2 due to an electron device placed in the vicinity of the positional deviation detection unit.

Further, in the above-described embodiment, the following further effects can be further acquired by the following configuration.

That is, in this embodiment, as described above, the feature point 11 is provided on the X-ray detection unit 2. Further, the optical feature point acquisition unit 4b is provided on the X-ray irradiation unit 1 and includes the imaging unit 13 for acquiring the position information on the feature point 11 by imaging the feature point 11. Thus, by imaging the feature point 11 by the imaging unit 13, it is possible to easily acquire the position of the feature point 11. Consequently, the positional deviation between the X-ray irradiation unit 1 and the X-ray detection unit 2 can be easily acquired.

In this embodiment, as described above, the X-ray detection unit 2 is placed between the subject 90 and the top board 10 on which the subject 90 is placed at the time of X-ray irradiation. Further, the feature point 11 is provided at the corner 2a of the X-ray detection unit 2. Thus, it is possible to place the feature point 11 at the position spaced apart from the center 2c of the X-ray detection unit 2. Therefore, when the X-ray detection unit 2 is placed between the subject 90 and the top board 10, it is possible to suppress the feature point 11 from being covered by the subject 90. As a result, it is possible to suppress that the feature point 11 cannot be imaged by the imaging unit 13 because the feature point 11 is covered by the subject 90.

Further, in this embodiment, as described above, the feature point 11 includes the planar marker 110a including three or more recognition points 12 to be recognized by the imaging unit 13. The X-ray detection unit 2 is provided with at least one planar marker 110a. As a result, since the planar marker 110a includes three or more recognition points 12, the position of the center 2c of the X-ray detection unit 2 can be easily acquired by imaging the planar marker 110a provided on the X-ray detection unit 2 with the imaging unit 13. As a result, the positional deviation between the X-ray irradiation unit 1 and the X-ray detection unit 2 can be easily acquired by capturing the image of the planar marker 110a provided on the X-ray detection unit 2 by the imaging unit 13.

In this embodiment, as described above, the planar marker 110a includes at least one of a printed figure and an outline of the X-ray detection unit 2. Here, for example, in a configuration using an electromagnetic coil as the feature point 11, a power supply, etc., for applying a current to the electromagnetic coil is required. Thus, the number of components increases. However, in a case in which one of the printed figure, and the outline of the X-ray detection unit 2 is the feature point 11, the printed figure can be placed on the X-ray detection unit 2 or the X-ray detection unit 2 itself can be the feature point 11. Therefore, by configuring as described above, for example, as compared with the configuration using an electromagnetic coil as the feature point 11, it is possible to suppress the increase in the number of components.

Further, in this embodiment, as described above, the imaging unit 13 is configured to image the subject 90 by visible light. The notification unit 4c includes the display unit 14 for displaying the positional deviation together with the image 20 of the subject 90 captured by the imaging unit 13. With this, since the positional deviation is displayed together with the image 20 of subject 90 on the display unit 14, it is possible to make the operator visually grasp the positional deviation between the X-ray irradiation unit 1 and the X-ray detection unit 2. As a result, the positional deviation can be visually grasped, and therefore the convenience of the operator when the operator adjusts the positional deviation can be improved.

Further, in this embodiment, as described above, the positional deviation acquisition unit 4a is configured to acquire the positional deviation and the angular deviation between the X-ray irradiation unit 1 and the X-ray detection unit 2, based on the position information. The display unit 14 displays the axis 30 indicating the center 30a of the irradiation range of the X-rays irradiated from the X-ray irradiation unit 1 and the axis 31 indicating the center 2c of the X-ray detection unit 2, together with the image 20 of the subject 90. Thus, the display unit 14 displays the positional deviation and the angular deviation between the X-ray irradiation unit 1 and the X-ray detection unit 2. Therefore, the image 20 of the subject 90, the axis 30 indicating the center 30a of the irradiation range of the X-rays, and the axis 31 indicating center 2c of the X-ray detection unit 2 can be displayed as the guides for the alignment between the X-ray irradiation unit 1 and the X-ray detection unit 2. Thus, the operator can perform the alignment between the X-ray irradiation unit 1 and the X-ray detection unit 2 with the image 20 of the subject 90, the axis 30 indicating the center 30a of the irradiation range of the X-rays, and the axis 31 indicating the center 2c of the X-ray detection unit 2 as guides. Consequently, the operator can easily perform the alignment between the X-ray irradiation unit 1 and the X-ray detection unit 2.

In this embodiment, as described above, the optical feature point acquisition unit 4b and the display unit 14 are provided on the X-ray irradiation unit 1 in an attachable and detachable manner. The feature point 11 includes the marker member 11a. The marker member 11a is provided on the X-ray detection unit 2. Thus, since the optical feature point acquisition unit 4b and the display unit 14 are configured to be mountable on the X-ray irradiation unit 1, it is possible to retrofit the positional deviation detection unit 4 to a pre-existing X-ray imaging apparatus, Further, since the feature point 11 includes the marker member 11a, it is possible to retrofit the feature point 11 to an X-ray detector of an existing X-ray imaging apparatus. As a consequence, the positional deviation detection unit 4 can be retrofitted to an existing X-ray imaging apparatus, and therefore it is particularly useful to apply the present invention to an existing X-ray imaging apparatus.

Modifications

It should be understood that the embodiments disclosed here are examples in all respects and are not restrictive. The scope of the present invention is shown by the scope of claims rather than the descriptions of the embodiments described above, and includes all changes (modifications) within the meaning of equivalent to the claims.

For example, in the above-described embodiment, an example is shown in which it is configured such that the feature point 11 (marker member 11a) to be detected by the optical feature point acquisition unit 4b includes the planar marker 110a, but the present invention is not limited thereto. In the present invention, for example, the feature point 11 (marker member 11a) to be detected by the optical feature point acquisition unit 4b according to a first modification may be a point-like marker 110b (see FIG. 11).

Figure 10:
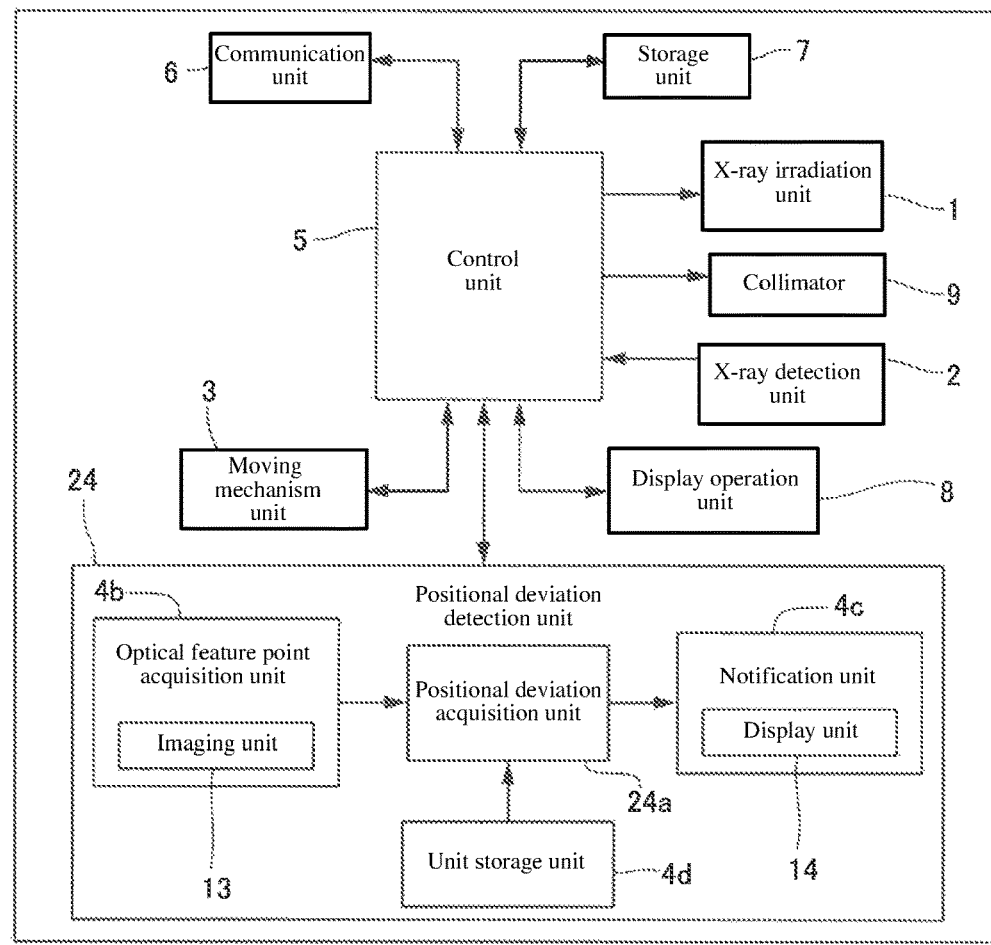
FIG. 10 is a block diagram showing an entire configuration of an X-ray imaging apparatus according to a first modification.

As shown in FIG. 10, the X-ray imaging apparatus 200 according to the first modification differs from the X-ray imaging apparatus 100 according to the above-described embodiment in that it is provided with a positional deviation detection unit 24 instead of the positional deviation detection unit 4.

The positional deviation detection unit 24 differs from the positional deviation detection unit 4 according to the above-described embodiment in that it is provided with a positional deviation acquisition unit 24a instead of the positional deviation acquisition unit 4a.

Figure 11:
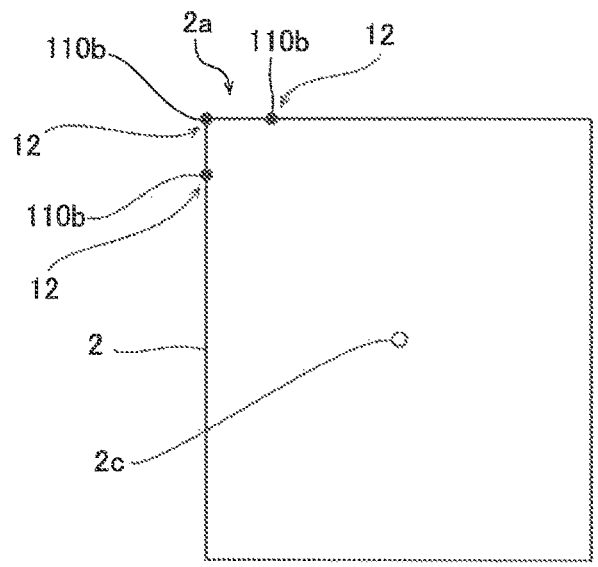
FIG. 11 is a schematic diagram for explaining a configuration in which a positional deviation acquisition unit according to a first modification acquires a positional deviation between an X-ray irradiation unit and an X-ray detection unit based on a feature point.

The positional deviation acquisition unit 24a is configured to acquire the positional deviation between the X-ray irradiation unit 1 and the X-ray detection unit 2, based on the position information on the point-like marker 110b (see FIG. 11).

As shown in FIG. 11, the feature point 11 includes a point-like marker 110b constituted by one recognition point 12 to be recognized by the imaging unit 13. As shown in FIG. 11, at least three point-like markers 110b are provided on the X-ray detection unit 2. As shown in FIG. 11, in the first modification, the X-ray detection unit 2 is provided with three point-like markers 110b. The point-like marker 110b includes at least one of a point light source, and a retroreflective member that reflects illumination light in the incident direction. Note that the point-like marker 110b may have a configuration in which a dot is printed on the surface of the X-ray detection unit 2 or a dot-shaped sealing member is attached to the surface of the X-ray detection unit 2. In the example shown in FIG. 11, the point-like marker 110*b* is a point light source. Note that, when using a retroreflective member as the point-like marker 110*b*, it may be configured such that a light source may be provided to the imaging unit 13, or light emitted from a room illumination and reflected by a retroreflective member is detected.

The point-like marker 110*b* is provided at a predetermined position on the X-ray detection unit 2. That is, the point-like marker 110*b* is provided on the X-ray detection unit 2 so that the position coordinate when the center 2*c* of the X-ray detection unit 2 is set as the origin becomes a preset position coordinate. Therefore, the positional deviation acquisition unit 24*a* can acquire the positional deviation between the X-ray irradiation unit 1 and the X-ray detection unit 2 by acquiring the position coordinate of the point-like marker 110*b*.

Figure 12:
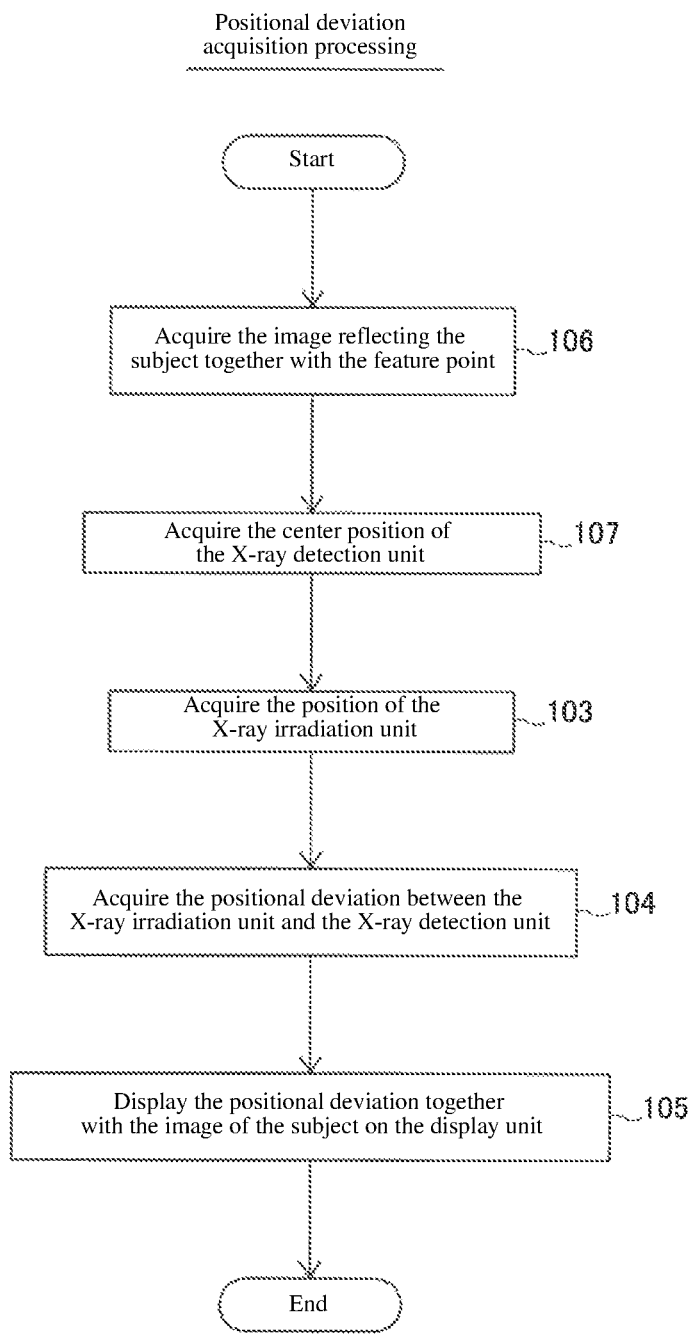
FIG. 12 is a flowchart for explaining processing in which a positional deviation acquisition unit according to a first modification acquires a positional deviation between an X-ray irradiation unit and an X-ray detection unit.

Next, referring to FIG. 12, the processing will be described in which the positional deviation detection unit 24 acquires the positional deviation between the X-ray irradiation unit 1 and the X-ray detection unit 2. Note that the same processing as that of the processing performed by the positional deviation detection unit 4 according to the above-described embodiment will be denoted by the same reference numeral, and the detailed description thereof will be omitted.

In Step 106, the imaging unit 13 acquires the image 20 reflecting the subject 90 together with the feature point 11 (point-like marker 110*b*).

In Step 107, the positional deviation acquisition unit 24*a* acquires the position of the center 2*c* of the X-ray detection unit 2 based on the image 20. Specifically, the positional deviation acquisition unit 24*a* acquires the position information on the center 2*c* of the X-ray detection unit 2, based on the position information on the point-like marker 110*b* (recognition point 12).

Thereafter, the processing proceeds from Step 103 to Step 105. The positional deviation acquisition unit 24*a* makes the display unit display the acquired positional deviation between the X-ray irradiation unit 1 and the X-ray detection unit 2, together with the image 20 of the subject 90. Thereafter, the processing ends.

In the first modification, as described above, the feature point 11 includes the point-like marker 110*b* configured by one recognition point 12 to be recognized by the imaging unit 13, and the X-ray detection unit 2 is provided with at least three point-like markers 110*b*. Thus, for example, as compared with the case of using an electromagnetic coil as the feature point 11, it is possible to suppress the size of the feature point 11 from being increased. Consequently, even in a case where the region capable of placing the feature point in the X-ray detection unit 2 is small in the X-ray detection unit, it becomes possible to place the point-like marker 110*b*, and therefore the flexibility of designing the X-ray detection unit 2 can be improved.

Further, in the first modification, as described above, the point-like marker 110*b* includes at least one of the point light source and the retroreflective member that reflects illumination light in the incident direction. Thus, in the case of placing the point light source as the point-like marker 110*b*, by detecting the light emitted from the point light source, it is possible to easily acquire the position of the point-like marker 110*b*. Further, in the case of placing a retroreflective member as the point-like marker 110*b*, by detecting the illumination light reflected by the retroreflective member, it is possible to easily acquire the position of the point-like marker 110*b*. Consequently, by placing a point light source or a retroreflective member as the point-like marker 110*b*, it is possible to easily acquire the position of the X-ray detection unit 2.

Further, in the above-described embodiment, an example is shown in which it is configured such that the feature point 11 is provided at the corner 2*a* of the X-ray detection unit 2, but the present invention is not limited thereto. For example, like the second modification shown in FIG. 13, the feature point 11 may be provided at a position spaced apart from the corner 2*a* of the X-ray detection unit 2.

Figure 13:
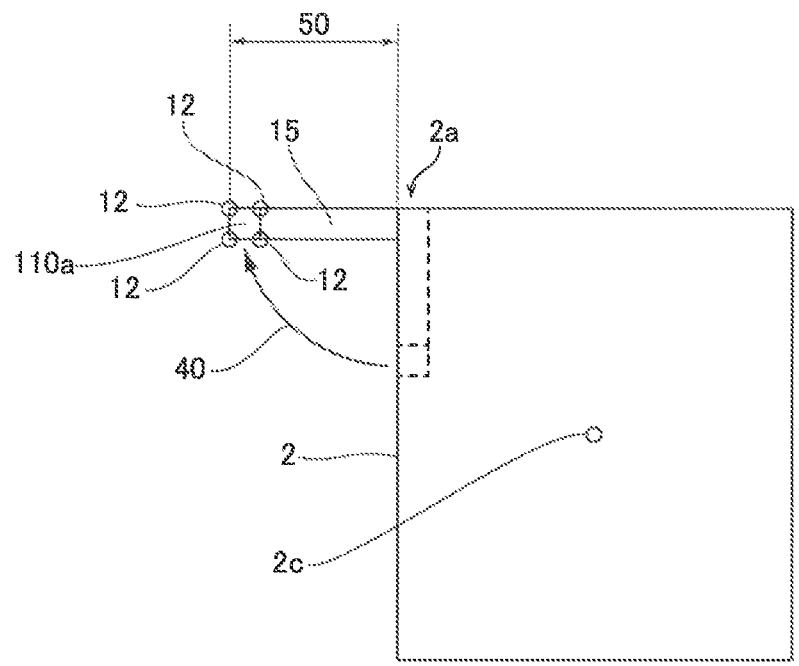
FIG. 13 is a schematic diagram for explaining a feature point provided on an X-ray detection unit according to a second modification.

Specifically, like a second modification shown in FIG. 13, the feature point 11 (planar marker 110*a*) may be movably provided on the X-ray detection unit 2 at a position spaced apart from the corner 2*a* of the X-ray detection unit 2 by a predetermined distance 50. In the embodiment shown in FIG. 13, the planar marker 110*a* is provided on the support member 15. The support member 15 is rotatably provided at the corner 2*a* of the X-ray detection unit 2. Specifically, the support member 15 is provided at the corner 2*a* of the X-ray detection unit 2 so as to be rotatable in the direction indicated by the arrow 40.

The movement (rotation) of the support member 15 in the direction indicated by the arrow 40 causes the feature point 11 (planar marker 110*a*) to be moved to a position spaced apart from the corner 2*a* of the X-ray detection unit 2 by the predetermined distance 50.

In the second modification, as described above, the feature point 11 is provided to the X-ray detection unit 2 in a movable manner at the position spaced apart from the corner 2*a* of the X-ray detection unit 2 by the predetermined distance 50. With this, since the feature point 11 is placed at the position spaced apart from the corner 2*a* of the X-ray detection unit 2 by the distance 50, even in a case where the entire surface of the X-ray detection unit 2 is covered by the subject 90, it is possible to suppress the feature point 11 from being covered by the subject 90. It is possible to more effectively prevent the problem that the feature point 11 is covered by the subject 90 and therefore the feature point 11 cannot be imaged by the imaging unit 13.

Figure 14:
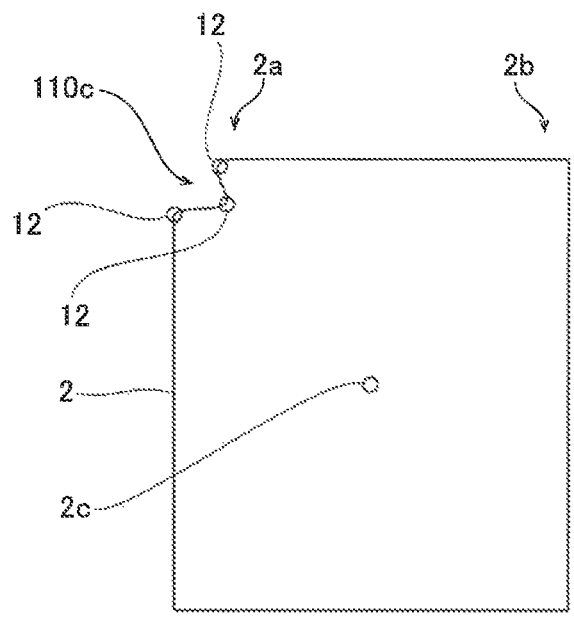
FIG. 14 is a schematic diagram for explaining a configuration of an X-ray detection unit according to a third modification.

Further, in the above-described embodiment, an example is shown in which it is configured such that the planar marker 110*a* is a printed figure, but the present invention is not limited thereto. For example, like a third modification shown in FIG. 14, the planar marker may be an outline of the X-ray detection unit 2. Note that in a case where the outline of the X-ray detection unit 2 is a planar marker, it is preferable that the corner 2*a* of the X-ray detection unit 2 differ in shape from the corner 2*b* of the X-ray detection unit 2 as shown in FIG. 14. As a result, the back and front sides of the X-ray detection unit 2 can be distinguished.

In the example shown in FIG. 14, by forming the recess 110*c* at the corner 2*a* of the X-ray detection unit 2, the shape of the corner 2*a* of the X-ray detection unit 2 is differentiated from the shape of the corner 2*b* of the X-ray detection unit 2. In a third modification, each corner of the recess 110*c* serves as the recognition point 12.

In the above-described embodiment, an example is shown in which it is configured such that the optical feature point acquisition unit 4*b* includes the imaging unit 13, but the present invention is not limited thereto. For example, it may be configured such that the optical feature point acquisition unit 4*b* emits laser light, detects the laser light reflected by an object, and detects the feature point 11 by the time required to detect the reflected laser beam. That is, the optical feature point acquisition unit 4*b* may be composed of an illumination unit of the laser light, a detection unit for detecting the laser light, and a time measuring unit for measuring the detection time. In other words, the optical feature point acquisition unit 4b may be configured as a so-called Lidar (Light Detection and Ranging).

Further, in the above-described embodiment, an example is shown in which it is configured such that the imaging unit 13 images the subject 90 by visible light, but the present invention is not limited thereto. For example, the imaging unit may be configured to image the subject 90 by a long-wavelength-side infrared ray among light in a wavelength band adjoining the visible light region. Further, the imaging unit may be configured to image the subject 90 by short-wavelength-side UV light among light in a wavelength band adjoining visible light region. In a case where the imaging unit images the subject 90 by infrared ray or ultraviolet ray, a light source for emitting infrared ray or ultraviolet ray may be provided.

Further, in the above-described embodiment, an example is shown in which the feature point 11 is provided at the corner 2a of the X-ray detection unit 2, but the present invention is not limited thereto. The feature point 11 may be provided at a position other than the corner 2a of the X-ray detection unit 2. However, in a configuration in which the feature point 11 is provided at a position other than the corner 2a of the X-ray detection unit 2, it is conceivable that the feature point 11 is covered by the subject 90. Therefore, the feature point 11 is preferably provided at the corner 2a of the X-ray detection unit 2.

In the above-described embodiment, an example is shown in which it is configured such that two planar markers 110a are provided on the X-ray detection unit 2, but the present invention is not limited thereto. It may be configured such that one planar marker 110a is provided or three planar markers 110a are provided. As long as the number is one or more, the number of the planar marker 110a is not limited.

Further, in the above-described embodiment, an example is shown in which it is configured such that the positional deviation detection unit 4 is mounted on the X-ray irradiation unit 1 in an attachable and detachable manner, but the present invention is not limited thereto. For example, the positional deviation detection unit may be fixedly provided with respect to the X-ray irradiation unit 1. That is, the positional deviation detection unit may be provided as an embedded type unit with respect to the X-ray irradiation unit 1. In other words, the positional deviation detection unit may be provided on the X-ray irradiation unit 1 as a so-called built-in unit.

Further, in the above-described embodiment, an example is shown in which it is configured such that the display unit 14 of the positional deviation detection unit 4 is provided on the X-ray irradiation unit 1, but the present invention is not limited thereto. For example, the display unit 14 may be provided on a separate device, such as, a smartphone and a tablet terminal, separately from the X-ray irradiation unit 1. In a case where the display unit 14 is provided separately from the X-ray irradiation unit 1, the positional deviation detection unit 4 may be configured to transmit the image 20 to the display unit 14 by, for example, a communication unit.

Further, in the above-described embodiment, an example is shown in which the notification unit 4c includes the display unit 14, but the present invention is not limited thereto. For example, the notification unit 4c may be configured to notify a positional deviation between the X-ray irradiation unit 1 and the X-ray detection unit 2 by voice. That is, the notification unit 4c may include, for example, a speaker. Further, the notification unit 4c may be configured to notify a positional deviation by light. In other words, the notification unit may include a light emitting unit. In a case in which the notification unit is configured to notify a positional deviation by light, it may be configured to notify the degree of the positional deviation by the difference in light emission color.

Further, in the above-described embodiment, an example is shown in which it is configured such that the optical feature point acquisition unit 4b is provided on the X-ray irradiation unit 1 and the feature point 11 is provided on the X-ray detection unit 2, the present invention is not limited thereto. For example, it may be configured such that the feature point 11 is provided on the X-ray irradiation unit 1 and the optical feature point acquisition unit 4b is provided on the X-ray detection unit 2.

Further, in the above-described embodiment, an example is shown in which it is configured such that the X-ray imaging apparatus 100 is moved to a hospital room in which the patient is present at the time of doctor's rounds to perform imaging, but the present invention is not limited thereto. For example, the X-ray imaging apparatus may be provided in an examination room. In a case where the X-ray imaging apparatus is provided in an examination room, the moving mechanism unit may be configured to movably support the X-ray irradiation unit rather than the entire device.

Further, in the above-described embodiment, an example is shown in which it is configured such that the positional deviation acquisition unit 4a acquires the deviation in the rotation direction within the plane of the image 20 as the angular deviation between the X-ray irradiation unit 1 and the X-ray detection unit 2, but the present invention is not limited thereto. For example, it may be configured such that the positional deviation acquisition unit acquires the angular deviation about the axis of the X-direction and the angular deviation about the axis of Y-direction. That is, the angular deviation between the X-ray irradiation unit 1 and the X-ray detection unit 2 may include the angular deviation about the axis of the X-direction and the angular deviation about the axis of the Y-direction, in addition to the angular deviation about the axis of the Z-direction.

ASPECTS

It will be understood by those skilled in the art that the above-described exemplary embodiments are concrete examples of the following aspects.

(Item 1)

An X-ray imaging apparatus comprising:

an X-ray irradiation unit configured to emit X-rays to a subject;

an X-ray detection unit to be placed at the time of X-ray irradiation, the X-ray detection unit being configured to detect the X-rays emitted from the X-ray irradiation unit;

a moving mechanism unit configured to be movable in a state of supporting the X-ray irradiation unit;

an optical feature point acquisition unit provided on either one of the X-ray irradiation unit and the X-ray detection unit, the optical feature point acquisition unit being configured to optically detect a feature point provided on the other of the X-ray irradiation unit and the X-ray detection unit to acquire a position of the feature point;

a positional deviation acquisition unit configured to acquire a positional deviation of a relative position between the X-ray irradiation unit and the X-ray detection unit, based on the position of the feature point acquired by the optical feature point acquisition unit;

and a notification unit configured to perform a notification based on the positional deviation acquired by the positional deviation acquisition unit.

(Item 2)

The X-ray imaging apparatus as recited in the above-described Item 1,
wherein the feature point is provided on the X-ray detection unit, and
wherein the optical feature point acquisition unit is provided on the X-ray irradiation unit and includes an imaging unit for acquiring position information on the feature point by imaging the feature point.

(Item 3)

The X-ray imaging apparatus as recited in the above-described Item 2,
wherein the X-ray detection unit is placed between the subject and a top board on which the subject is placed at the time of X-ray irradiation, and
wherein the feature point is provided at a corner of the X-ray detection unit.

(Item 4)

The X-ray imaging apparatus as recited in the above-described Item 3,
wherein the feature point is provided on the X-ray detection unit in a movable manner at a position spaced apart from the corner of the X-ray detection unit by a predetermined distance.

(Item 5)

The X-ray imaging apparatus as recited in the above-described Item 2,
wherein the feature point includes a planar marker including three or more recognition points to be recognized by the imaging unit, and
wherein the X-ray detection unit is provided with at least one planar marker.

(Item 6)

The X-ray imaging apparatus as recited in the above-described Item 5,
wherein the planar marker includes at least either one of a printed figure and an outline of the X-ray detection unit.

(Item 7)

The X-ray imaging apparatus as recited in the above-described Item 2,
wherein the feature point includes a point-like marker configured by one recognition point to be recognized by the imaging unit, and
wherein the X-ray detection unit is provided with at least three of the point-like markers.

(Item 8)

The X-ray imaging apparatus as recited in the above-described Item 7,
wherein the point-like marker includes at least either one of a point light source and a retroreflective member that reflects illumination light in an incident direction.

(Item 9)

The X-ray imaging apparatus as recited in the above-described Item 2,
wherein the imaging unit is configured to image the subject by visible light, and
wherein the notification unit includes a display unit for displaying the positional deviation together with an image of the subject captured by the imaging unit.

(Item 10)

The X-ray imaging apparatus as recited in the above-described Item 9,
wherein the positional deviation acquisition unit is configured to acquire a positional deviation and an angular deviation between the X-ray irradiation unit and the X-ray detection unit, based on the position information, and
wherein the display unit is configured to display the positional deviation and the angular deviation between the X-ray irradiation unit and the X-ray detection unit by displaying an axis indicating a center of an irradiation range of the X-rays emitted from the X-ray irradiation unit and an axis indicating a center of the X-ray detection unit together with the image of the subject.

(Item 11)

The X-ray imaging apparatus as recited in the above-described Item 9,
wherein the optical feature point acquisition unit and the display unit are mounted on the X-ray irradiation unit in an attachable and detachable manner,
wherein the feature point includes a marker member, and
wherein the marker member is provided on the X-ray detection unit.

(Item 12)

A positional deviation detection unit for an X-ray imaging apparatus, the X-ray imaging apparatus being composed of an X-ray irradiation unit for irradiating a subject with X-rays, an X-ray detection unit to be arranged at the time of X-ray irradiation to detect the X-rays emitted from the X-ray irradiation unit, and a moving mechanism unit configured to be movable in a state of supporting the X-ray irradiation unit, the positional deviation detection unit comprising:
an optical feature point acquisition unit provided on either one of the X-ray irradiation unit and the X-ray detection unit, the optical feature point acquisition unit being configured to optically detect a feature point provided on the other of the X-ray irradiation unit and the X-ray detection unit to acquire a position of the feature point;
a positional deviation acquisition unit configured to acquire a positional deviation of a relative position between the X-ray irradiation unit and the X-ray detection unit, based on the position of the feature point acquired by the optical feature point acquisition unit; and
a notification unit configured to perform a notification based on the positional deviation acquired by the positional deviation acquisition unit.

The invention claimed is:

1. An X-ray imaging apparatus comprising:
an X-ray irradiation unit configured to emit X-rays to a subject;
an X-ray detection unit to be placed at the time of X-ray irradiation, the X-ray detection unit being configured to detect the X-rays emitted from the X-ray irradiation unit;
a moving mechanism unit configured to be movable in a state of supporting the X-ray irradiation unit;
an optical feature point acquisition unit provided on the X-ray irradiation unit, the optical feature point acquisition unit being configured to optically detect a feature point provided on the X-ray detection unit to acquire a position of the feature point;
a positional deviation acquisition unit configured to acquire a positional deviation including an angular deviation of a relative position between the X-ray irradiation unit and the X-ray detection unit, based on the position of the feature point acquired by the optical feature point acquisition unit;

a notification unit configured to perform a notification based on the positional deviation of the relative position between the X-ray irradiation unit and the X-ray detection unit acquired by the positional deviation acquisition unit; and a storage unit configured to store the X-ray detection unit, wherein the X-ray imaging apparatus is configured such that the entire X-ray imaging apparatus can be moved in a state that the X-ray detection unit is stored by the storage unit, wherein the X-ray detection unit has a rectangular shape with a short side and a long side, wherein the feature point is provided at at least one corner of the X-ray detection unit having the rectangular shape, wherein the optical feature point acquisition unit includes an imaging unit having an imaging center provided separately at a first predetermined distance from an optical axis of the x-rays emitted from the X-ray irradiation unit, wherein the positional deviation acquisition unit is configured to acquire the positional deviation of the X-ray irradiation unit and the X-ray detection unit based on an information of the first predetermined distance, and wherein the feature point is provided on the X-ray detection unit in a movable manner at a position spaced apart from the X-ray detection unit by a second predetermined distance.

2. The X-ray imaging apparatus as recited in claim 1, wherein the imaging unit acquires position information on the feature point by imaging the feature point.

3. The X-ray imaging apparatus as recited in claim 2, wherein the X-ray detection unit is placed between the subject and a top board on which the subject is placed at the time of X-ray irradiation.

4. The X-ray imaging apparatus as recited in claim 2, wherein the feature point includes a planar marker including three or more recognition points to be recognized by the imaging unit, and wherein the X-ray detection unit is provided with at least one planar marker.

5. The X-ray imaging apparatus as recited in claim 4, wherein the planar marker includes at least either one of a printed figure and an outline of the X-ray detection unit.

6. The X-ray imaging apparatus as recited in claim 2, wherein the feature point includes a point-like marker configured by one recognition point to be recognized by the imaging unit, and wherein the X-ray detection unit is provided with at least three of the point-like markers.

7. The X-ray imaging apparatus as recited in claim 6, wherein the point-like marker includes at least either one of a point light source and a retroreflective member that reflects illumination light in an incident direction.

8. The X-ray imaging apparatus as recited in claim 2, wherein the imaging unit is configured to image the subject by visible light, and wherein the notification unit includes a display unit for displaying the positional deviation together with an image of the subject captured by the imaging unit.

9. The X-ray imaging apparatus as recited in claim 8, wherein the positional deviation acquisition unit is configured to acquire a positional deviation and the angular deviation between the X-ray irradiation unit and the X-ray detection unit, based on the position information, and wherein the display unit is configured to display the positional deviation and the angular deviation between the X-ray irradiation unit and the X-ray detection unit by displaying an axis indicating a center of an irradiation range of the X-rays emitted from the X-ray irradiation unit and an axis indicating a center of the X-ray detection unit together with the image of the subject.

10. The X-ray imaging apparatus as recited in claim 8, wherein the optical feature point acquisition unit and the display unit are mounted on the X-ray irradiation unit in an attachable and detachable manner, wherein the feature point includes a marker member.

11. A positional deviation detection unit for an X-ray imaging apparatus, the X-ray imaging apparatus being composed of an X-ray irradiation unit for irradiating a subject with X-rays, an X-ray detection unit to be arranged at the time of X-ray irradiation to detect the X-rays emitted from the X-ray irradiation unit, and a moving mechanism unit configured to be movable in a state of supporting the X-ray irradiation unit, the positional deviation detection unit comprising:

an optical feature point acquisition unit provided on the X-ray irradiation unit, the optical feature point acquisition unit being configured to optically detect a feature point provided on the X-ray detection unit to acquire a position of the feature point;

a positional deviation acquisition unit configured to acquire a positional deviation including an angular deviation of a relative position between the X-ray irradiation unit and the X-ray detection unit, based on the position of the feature point acquired by the optical feature point acquisition unit; and a notification unit configured to perform a notification based on the positional deviation of the relative position between the X-ray irradiation unit and the X-ray detection unit acquired by the positional deviation acquisition unit, wherein the X-ray imaging apparatus further includes a storage unit configured to store the X-ray detection unit and is configured such that the entire X-ray imaging apparatus can be moved in a state that the X-ray detection unit is stored by the storage unit, wherein the X-ray detection unit has a rectangular shape with a short side and a long side, wherein the feature point is provided at at least one corner of the X-ray detection unit having the rectangular shape, wherein the optical feature point acquisition unit includes an imaging unit having an imaging center provided separately at a first predetermined distance from an optical axis of the x-rays emitted from the X-ray irradiation unit, wherein the positional deviation acquisition unit is configured to acquire the positional deviation of the X-ray irradiation unit and the X-ray detection unit based on an information of the first predetermined distance, and wherein the feature point is provided on the X-ray detection unit in a movable manner at a position spaced apart from the X-ray detection unit by a second predetermined distance.

\* \* \* \* \*